United States Patent
Dehn et al.

(10) Patent No.: US 10,414,707 B2
(45) Date of Patent: Sep. 17, 2019

(54) PROCESS FOR PRODUCING PRENOL AND PRENAL FROM ISOPRENOL

(71) Applicant: BASF SE, Ludwigshafen am Rhein (DE)

(72) Inventors: Martine Dehn, Ludwigshafen am Rhein (DE); Bernhard Brunner, Ludwigshafen am Rhein (DE); Klaus Ebel, Gorxheimertal (DE); Sabine Huber, Ludwigshafen am Rhein (DE)

(73) Assignee: BASF SE, Ludwigshafen Am Rhein (DE)

( * ) Notice: Subject to any disclaimer, the term of this patent is extended or adjusted under 35 U.S.C. 154(b) by 0 days.

(21) Appl. No.: 16/084,285

(22) PCT Filed: Mar. 14, 2017

(86) PCT No.: PCT/EP2017/055922
§ 371 (c)(1),
(2) Date: Sep. 12, 2018

(87) PCT Pub. No.: WO2017/157897
PCT Pub. Date: Sep. 21, 2017

(65) Prior Publication Data
US 2019/0077736 A1 Mar. 14, 2019

(30) Foreign Application Priority Data
Mar. 15, 2016 (EP) .................................... 16160410

(51) Int. Cl.
C07C 29/56 (2006.01)
C07C 45/38 (2006.01)
B01J 23/00 (2006.01)
B01J 21/04 (2006.01)
B01J 21/08 (2006.01)
B01J 23/44 (2006.01)
B01J 23/52 (2006.01)
C07C 33/03 (2006.01)
C07C 47/21 (2006.01)

(52) U.S. Cl.
CPC .............. C07C 29/56 (2013.01); B01J 21/04 (2013.01); B01J 21/08 (2013.01); B01J 23/44 (2013.01); B01J 23/52 (2013.01); C07C 45/38 (2013.01); C07C 33/03 (2013.01); C07C 47/21 (2013.01)

(58) Field of Classification Search
CPC ........... C07C 29/56; C07C 45/38; B01J 23/44
See application file for complete search history.

(56) References Cited

U.S. PATENT DOCUMENTS 8,263,813 B2 9/2012 Limbach et al.

FOREIGN PATENT DOCUMENTS

| WO | WO-2008037693 A1 | 4/2008 |
| WO | WO-2009106621 A1 | 9/2009 |
| WO | WO-2009106622 A1 | 9/2009 |

OTHER PUBLICATIONS

Feng, B., et al., "The functionalized poly(ethylene glycol) supported palladium nanoparticles as a highly efficient catalyst for aerobic oxidation of alcohols", Catalysis Communications, vol. 10, No. 11, (2009), pp. 1542-1546.
Hou, Z., et al., "Supported palladium nanoparticles on hybrid mesoporous silica: Structure/activity-relationship in the aerobic alcohol oxidation using supercritical carbon dioxide", Journal of Catalysis, vol. 258, No. 2, (2008), pp. 315-323.
International Search Report for PCT/EP2017/055922 dated May 16, 2017.
Karimi, B., et al., "Aerobic oxidation of alcohols using various types of immobilized palladium catalyst: the synergistic role of functionalized ligands, morphology of support, and solvent in generating and stabilizing nanoparticles", Green Chemistry, vol. 11, No. 1, (2009), pp. 109-119.
Larock, R., et al., "Oxidation of Allylic Alcohols to Unsaturated Carbonyl Compounds by Ruthenium Dioxide and Dioxygen/Ruthenium Dixoxide", Journal of Organic Chemistry, vol. 49, (1984), pp. 3435-3436.
Parlett, C., et al., "Support-Enhanced Selective Aerobic Alcohol Oxidation over Pd/Mesoporous Silicas", ACS Catalysis, vol. 1, (2011), pp. 636-640.
Written Opinion of the International Searching Authority for PCT/EP2017/055922 dated May 16, 2017.

Primary Examiner — Sikarl A Witherspoon
(74) Attorney, Agent, or Firm — Drinker Biddle & Reath LLP

(57) ABSTRACT

The present invention relates to a process for preparing 3-methyl-2-butenol (prenol) and 3-methyl-2-butenal (prenal) from 3-methyl-3-butenol (isoprenol), in which 3-methyl-3-butenol is subjected to a catalytic isomerization over a carbon-supported Pd catalyst in the presence of a gas mixture comprising 1% to 15% by volume of oxygen to obtain a first product mixture, and the first product mixture is subjected to an oxidative dehydrogenation over a Pd catalyst comprising $SiO_2$ and/or $Al_2O_3$ as support material, or over a carbon-supported Pd/Au catalyst in the presence of a gas mixture comprising 5% to 25% by volume of oxygen.

17 Claims, No Drawings

PROCESS FOR PRODUCING PRENOL AND PRENAL FROM ISOPRENOL

CROSS-REFERENCE TO RELATED APPLICATIONS

This application is a national stage application (under 35 U.S.C. § 371) of PCT/EP2017/055922, filed Mar. 14, 2017, which claims benefit of European Application No. 16160410.3, filed Mar. 15, 2016, both of which are incorporated herein by reference in their entirety.

BACKGROUND OF THE INVENTION

The present invention relates to a process for preparing 3-methyl-2-butenol (prenol) and 3-methyl-2-butenal (prenal) from 3-methyl-3-butenol (isoprenol). The process can be performed continuously or batchwise.

STATE OF THE ART

3-Methyl-2-butenol (prenol) and 3-methyl-2-butenal (prenal) are important materials of value since they are used as synthesis units in many preparation processes on the industrial scale. For example, they are especially suitable as starting materials for preparation of isoprenoid compounds. For instance, prenol and prenal are used inter alia for preparation of odorants, for example citral, or vitamins, for example vitamin E and vitamin A.

The prior art discloses various processes for preparing prenol or prenal.

WO 2008/037693 describes a multistage process for preparing citral, in which prenol inter alia is obtained by isomerization of 3-methyl-3-butenol (isoprenol) over a heterogeneous precious metal catalyst in the presence of hydrogen and prenal via an oxidative dehydrogenation of isoprenol in the gas phase with downstream basic isomerization. Specifically, the heterogeneous precious metal catalyst used in the process for preparing prenol is a Pd-comprising catalyst on a ceramic support additionally comprising selenium, giving prenol in a selectivity of 91% at a conversion of 55%, based on the isoprenol used. Prenal is conducted via an oxidative dehydrogenation in the presence of an oxygenous gas over a supported silver catalyst at a temperature of 450° C., giving prenal in a selectivity of 75.6%, at a conversion of 62.8%, based on the isoprenol used. The process described has the disadvantage that the isomerization of isoprenol forms isoamyl alcohol, which can be separated from the reaction mixture only with difficulty. Moreover, the oxidative dehydrogenation in the gas phase used for preparation of prenal is inconvenient and costly and, owing to the high reaction temperatures, leads only to inadequate selectivities.

WO 2009/106622 describes a process in which the isomerization of olefinically unsaturated alcohols proceeds under significantly milder conditions, by conducting it over a carbon-supported precious metal catalyst in an oxygenous atmosphere. In spite of the mild conditions, the isomerization of olefinically unsaturated alcohols proceeds in good yields and selectivities, meaning that the formation of by-products, especially the corresponding saturated alcohols, can be kept to a low level. What is specifically described is the partial isomerization of 3-methyl-3-butenol (isoprenol) to 3-methyl-2-butenol (prenol) at temperatures of 80° C. in the presence of a Pd catalyst on charcoal under air at elevated pressure, which also forms a small proportion of 3-methyl-2-butenal (prenal) as well as a mixture of isoprenol and prenol.

Processes for preparing olefinically unsaturated carbonyl compounds by oxidative dehydrogenation of unsaturated alcohols in which the oxidative dehydrogenation is conducted under relatively mild conditions in the liquid phase are known, for example, from ACS Catal. 2011, 1, 636-640; Catalysis Communications 2009, 10(11), 1542; Journal of Catalysis 2008, 258(2) and 315; Green Chemistry 2009, 11 (1), 109. In these processes, palladium catalysts in particular are used.

The prior art likewise describes the use of various ruthenium catalysts which enable oxidation of allylic alcohols under relatively mild conditions. For example, Larock and Veraprath in J. Org. Chem. 1984, 49, 3435-3436, describe the preparation of unsaturated aldehydes, including prenal, by oxidation of the corresponding allylic alcohols at 70° C. in 1,2-dichloroethane in the presence of 10% by weight of $RuO_2$ hydrate and an oxygen atmosphere, and in the presence of the antioxidant 2,6-di-tert-butyl-p-cresol.

The prior art likewise states that prenol, in the known oxidative dehydrogenation processes, can typically be much more easily oxidized to prenal than isoprenol. For example, Parlett et al., ACS Catal. 2011, 1, 636-640, describes a process for oxidative dehydrogenation of allylic alcohols under mild conditions in the presence of various Pd catalysts on mesoporous silicon dioxide and atmospheric oxygen. They succeeded, inter alia, in oxidizing prenol in toluene at 90° C. in the presence of 0.5% by weight of a Pd catalyst on mesoporous $SiO_2$, obtaining prenal in a selectivity of 90% at a conversion of 27% after 24 h. By contrast, isoprenol was found to be unreactive under these reaction conditions.

WO 2009/106621 describes a process for preparing olefinically unsaturated carbonyl compounds by oxidative dehydrogenation of unsaturated alcohols in an oxygenous atmosphere at temperatures in the range from 50 to 240° C. and in the presence of a gold catalyst on a basic support, optionally comprising further precious metals as well as gold. What is specifically described is the preparation of 3-methyl-2-butenal (prenal) from 3-methyl-3-butenol (isoprenol), with preferential formation of 3-methyl-2-butenal (prenal) and not 3-methyl-3-butenal (isoprenal) owing to the use of basic support materials, and hence no need to conduct any downstream isomerization. In addition, WO 2009/106621 teaches that the conversion rate can be enhanced when isoprenol/prenol mixtures are used as starting material for the oxidative dehydrogenation. In this process, however, diluents are used, for example xylene, which reduces its attractiveness for industrial processes.

There is therefore a need for an improved process for preparing prenal and prenol from isoprenol, by which the above-described disadvantages that arise from the low reactivity of isoprenol with respect to the oxidative dehydrogenation can be overcome.

It is thus an object of the present invention to provide a process which enables the preparation of 3-methyl-2-butenol (prenol) and 3-methyl-2-butenal (prenal) from 3-methyl-3-butenol (isoprenol) under mild reaction conditions, especially low reaction temperatures, in which high conversion rates can be achieved in spite of the low reactivity of isoprenol with respect to oxidative dehydrogenation. The 3-methyl-2-butenol (prenol) and 3-methyl-2-butenal (prenal) are to be obtained in the form of compositions comprising prenol and prenal in very similar molar amounts. Moreover, the process is to enable the preparation of prenol and prenal in high total selectivity, and the formation of by-products that are difficult to remove is to be minimized. The process should additionally be suitable for a continuous process regime.

This object is surprisingly achieved by a process for preparing a composition comprising 3-methyl-2-butenol and 3-methyl-2-butenal, in which
i) 3-methyl-3-butenol is subjected to a catalytic isomerization over a carbon-supported Pd catalyst in the presence of a gas mixture comprising 1% to 15% by volume of oxygen to obtain a first product mixture comprising at least 40% by weight of 3-methyl-2-butenol, at least 5% by weight of 3-methyl-3-butenol and 0% to 15% by weight of 3-methyl-2-butenal, based on the total weight of the first product mixture,
ii) the first product mixture obtained in step i) is subjected to an oxidative dehydrogenation over a Pd catalyst comprising $SiO_2$ and/or $Al_2O_3$ as support material, or over a carbon-supported Pd/Au catalyst in the presence of a gas mixture comprising 5% to 25% by volume of oxygen, to obtain a second product mixture which is enriched in 3-methyl-2-butenal and depleted in 3-methyl-2-butenol compared to the first product mixture, where the molar ratio of 3-methyl-2-butenol to 3-methyl-2-butenal in the second product mixture is in the range from 75:25 to 35:65.

It has been found that a reaction output from a catalytic isomerization of isoprenol can advantageously be used directly in the oxidative dehydrogenation without intermediate purification, optionally after removal of the catalyst. The reactivity, i.e. the conversion, of the isomerization outputs used in the oxidative dehydrogenation is comparable here to the use of pure prenol, with even higher selectivities for prenol and prenal being achieved overall.

In addition, it has been found that the reactivity and selectivity in the oxidative dehydrogenation can additionally be enhanced by additions of base.

The invention therefore further provides a process as defined above, wherein the oxidative dehydrogenation in step ii) is additionally conducted in the presence of a base.

The invention further relates to the continuous performance of the process as defined above and hereinafter.

DESCRIPTION OF THE INVENTION

The process of the invention has at least one of the following advantages:
- The process enables the preparation of prenol and prenal in high total selectivities.
- The process of the invention can achieve high conversion rates even under mild reaction conditions, which means that the formation of by-products that are difficult to remove can be largely or even completely avoided.
- The process of the invention can give compositions comprising prenol and prenal in similar molar amounts.
- The process is easy to perform in spite of the two-stage reaction regime, since complex intermediate purifications in particular are not required.
- In the process, it is possible to largely or completely dispense with the use of external diluents, which leads to significantly improved space-time yields in conjunction with the high conversion rates.
- The process can advantageously be performed continuously.
- Owing to the abovementioned features, the process of the invention is suitable for preparation of prenol and prenal on the industrial scale and is additionally notable for advantageous economic viability.

Step i):

In step i) of the process of the invention, 3-methyl-3-butenol (isoprenol) is isomerized to 3-methyl-2-butenol (prenol). According to the invention, the isomerization is effected over a carbon-supported Pd catalyst in the presence of a gas mixture comprising 1% to 15% by volume of oxygen.

The catalytic isomerization can be performed either in the liquid phase or in the gas phase, the catalytic isomerization preferably being effected in the liquid phase.

The catalytic isomerization is typically effected in the presence of a gas mixture comprising 1% to 15% by volume of oxygen, i.e. in the presence of an oxygenous atmosphere. The gas mixture comprising 1% to 15% by volume of oxygen can be supplied to the reaction zone, for example, by a single injection prior to or on commencement of the reaction, by repeated injection during the reaction, or by continuous introduction over the entire course of the reaction. Preferably, in step ii) of the process of the invention, the oxygenous gas mixture is supplied to the reaction zone by continuous introduction over the entire course of the reaction.

Typically, the gas mixture used in step i) of the process of the invention comprises an oxygen content in the range from 1% to 15% by volume, preferably from 2% to 12% by volume and especially from 3% to 10% by volume.

In a particularly preferred embodiment of step i) of the process of the invention, the oxygenous atmosphere is exchanged by supplying an oxygen-enriched gas mixture and removing an oxygen-depleted gas mixture. The supply and removal of the oxygen-enriched and oxygen-depleted gas mixtures can be effected successively or simultaneously. Preferably, the exchange of the oxygenous atmosphere is performed repeatedly, and the total amount of oxygenous gas mixture exchanged corresponds at least to the volume of the amount of gas present in the reaction zone. More preferably, the total amount of oxygenous gas mixture exchanged corresponds to several times the volume, for example 10 times the volume, of the amount of gas present in the reaction zone. The exchange can be effected stepwise or continuously. Preferably, the oxygenous atmosphere is exchanged continuously.

If the oxygenous atmosphere is exchanged continuously, the exchange rate of the oxygenous gas mixture in the catalytic isomerization is typically in the range from 1 to 200 L/h, especially in the range from 3 to 120 L/h, especially in the range from 5 to 80 L/h, based on 100 g of the isoprenol used.

On completion of catalytic isomerization in step i), a first product mixture is obtained, comprising not only 3-methyl-2-butenol (prenol) but both 3-methyl-3-butenol (isoprenol) and optionally small amounts of 3-methyl-2-butenal (prenal).

In general, the first product mixture obtained in step i) of the process of the invention comprises at least 40% by weight of 3-methyl-2-butenol, at least 5% by weight of 3-methyl-3-butenol and 0% to 15% by weight of 3-methyl-2-butenal.

Preferably, the first product mixture obtained in step i) comprises 40% to 80% by weight, more preferably 45% to 70% by weight, of 3-methyl-2-butenol.

Preferably, the first product mixture obtained in step i) comprises 0% to 15% by weight, more preferably 5% to 10% by weight, of 3-methyl-2-butenal.

Preferably, the first product mixture obtained in step i) comprises 5% to 59% by weight, more preferably 20% to 50% by weight, of 3-methyl-3-butenol.

In a preferred embodiment of the process of the invention, the first product mixture obtained in step i) consists of
  i.1 40% to 80% by weight of 3-methyl-2-butenol,
  i.2 0% to 15% by weight of 3-methyl-2-butenal,
  i.3 5% to 59% by weight of 3-methyl-3-butenol and
  i.4 0% to 10% by weight of compounds other than i.1, i.2 and i.3.

In a particularly preferred embodiment of the process of the invention, the first product mixture obtained in step i) consists of
  i.1 45% to 70% by weight of 3-methyl-2-butenol,
  i.2 5% to 10% by weight of 3-methyl-2-butenal,
  i.3 20% to 50% by weight of 3-methyl-3-butenol and
  i.4 0% to 5% by weight of compounds other than i.1, i.2 and i.3.

The total proportion of 3-methyl-2-butenol, 3-methyl-2-butenal and 3-methyl-3-butenol in the first product mixture is typically at least 80% by weight, preferably at least 85% by weight, more preferably at least 90% by weight or more, for example at least 92% by weight, based on the total weight of the first product mixture.

According to the invention, the isomerization in step i) takes place in the presence of a carbon-supported Pd catalyst, i.e. a Pd catalyst comprising a support material based on carbon (C), for example activated carbon. Various types of charcoal or various types of graphite as known to the person skilled in the art and described in the literature are mentioned merely as examples of such materials.

Suitable carbon-based support materials in principle are all carbon materials known to the person skilled in the art for such uses. The support materials may preferably be used in the form of shaped bodies, granules, strands, pellets, spall, tablets or prills. The BET surface area of the support materials (25° C.) is typically in the range from 1 to 10 000, preferably from 10 to 5000, m²/g, but is uncritical in most cases for the process of the invention.

The Pd content of the carbon-supported Pd catalyst used in the catalytic isomerization is typically in the range from 0.1% to 20% by weight, preferably in the range from 0.5% to 15% by weight and especially in the range from 1% to 10% by weight, based on the total weight of the carbon-supported Pd catalyst.

Typically, the amount of the carbon-supported Pd catalyst used in the catalytic isomerization is in the range from 0.1% to 20% by weight, preferably in the range from 0.2% to 10% by weight, more preferably in the range from 0.5% to 5% by weight, based on the amount of isoprenol present in the reaction mixture.

The catalytic isomerization is typically performed at a pressure in the range from 1 to 100 bar, preferably in the range from 1 to 50 bar, especially in the range from 2 to 20 bar.

Typically, the reaction temperature in the catalytic isomerization is in the range from 20 to 150° C., preferably in the range from 40 to 120° C. and especially in the range from 50 to 110° C.

The catalytic isomerization can be effected in the presence or absence of an external solvent.

If the catalytic isomerization is effected in the presence of an external solvent, this is typically an inert organic solvent. In the context of the present invention, an inert solvent is understood to mean a solvent which does not enter into any reaction with the compounds and materials involved in the isomerization under the reaction conditions chosen.

Suitable inert solvents are, for example, aliphatic hydrocarbons such as pentane, hexane, heptane, ligroin, petroleum ether or cyclohexane, halogenated hydrocarbons such as dichloromethane, trichloromethane, tetrachloromethane, aromatic hydrocarbons such as benzene, toluene, xylenes, halogenated aromatic hydrocarbons such as chlorobenzene, dichlorobenzenes, ethers such as diethyl ether, methyl tert-butyl ether, dibutyl ether, diphenyl ether, tetrahydrofuran or 1,4-dioxane, and mixtures thereof. Particularly suitable examples are toluene, o-xylene, p-xylene, tetrahydrofuran, 1,4-dioxane or diphenyl ether.

Preference is given to performing the catalytic isomerization without addition of an external solvent.

The catalytic isomerization can be performed either in batchwise or continuous mode. Preference is given to performing the catalytic isomerization in continuous mode.

Typically, the catalytic isomerization of 3-methyl-3-butenol to 3-methyl-2-butenol is run up to a conversion of 30% to 80%, preferably up to a conversion of 35% to 75%, especially of 40% to 70%, based on the 3-methyl-3-butenol used.

The 3-methyl-3-butenol used for catalytic isomerization is typically commercially available 3-methyl-3-butenol or 3-methyl-3-butenol which is obtained as a waste stream in the recovery of materials of value, for example in the recovery of citral, and mixtures thereof. Commercially available 3-methyl-3-butenol can be synthesized on the industrial scale, for example from formaldehyde and isobutene, and is thus a cheap and readily available chemical starting material.

The first product mixture obtained in step i) of the process of the invention is also referred to hereinafter as "output from the catalytic isomerization". The first product mixture obtained in step i) of the process of the invention is typically used in the oxidative dehydrogenation in step ii) or, in continuous mode, fed to step ii), optionally after removal of the catalyst followed by a further purification, for example a distillative purification, or optionally after removal of the catalyst without any further purification.

Preferably, the output from the catalytic isomerization, optionally after removal of the catalyst, is used without further purification in the oxidative dehydrogenation in step ii) or, in continuous mode, fed to step ii).

Step ii):

The oxidative dehydrogenation in step ii) of the process of the invention is generally conducted in the presence of a Pd catalyst comprising $SiO_2$, $Al_2O_3$ or mixtures of $SiO_2$ and $Al_2O_3$ as support material, or in the presence of a carbon-supported Pd/Au catalyst.

Preferably, the Pd catalyst used in the oxidative dehydrogenation is a $SiO_2$— or $SiO_2/Al_2O_3$-supported Pd catalyst, especially a $SiO_2/Al_2O_3$-supported Pd catalyst.

Preferably, the carbon-supported Pd/Au catalyst used in the oxidative dehydrogenation is, i.e. a Pd/Au catalyst comprising a support material based on carbon (C), for example activated carbon. With regard to the activated carbons suitable as support material for this purpose, reference is made to the remarks made above in connection with the carbon-supported Pd catalyst.

The metal content of the Pd catalyst and/or Pd/Au catalyst used in step ii) of the process of the invention is not subject to any particular restriction. Preferably, the metal content of the Pd catalyst or Pd/Au catalyst used in step ii) of the process of the invention is in the range from 0.1% to 25% by weight, preferably in the range from 0.5% to 15% by weight and especially in the range from 2% to 10% by weight.

The Pd content of the Pd/Au catalyst used in step ii) of the process of the invention is typically in the range from 0.5% to 15% by weight, preferably in the range from 1% to 10% by weight and especially in the range from 2% to 7% by weight, based on the total weight of the carbon-supported Pd/Au catalyst.

The Au content of the Pd/Au catalyst used in step ii) of the process of the invention is typically in the range from 0.1% to 10% by weight, preferably in the range from 0.5% to 7% by weight and especially in the range from 1% to 5% by weight, based on the total weight of the carbon-supported Pd/Au catalyst.

The weight ratio of Pd to Au in the Pd/Au catalyst used in step ii) is typically in the range from 1:50 to 31, preferably in the range from 1:20 to 2:1, especially in the range from 1:10 to 1.2:1.

The $SiO_2$—, $Al_2O_3$— or $SiO_2/Al_2O_3$-supported Pd catalysts used in accordance with the invention or the carbon-supported Pd/Au catalysts used in accordance with the invention can be prepared by processes that are known to those skilled in the art and are described in the literature.

Typically, the amount of the Pd catalyst or Pd/Au catalyst used in the oxidative dehydrogenation is in the range from 0.1% to 20% by weight, preferably in the range from 0.2% to 10% by weight, more preferably in the range from 0.4% to 5% by weight, based on the total weight of the reaction mixture for the oxidative dehydrogenation.

The oxidative dehydrogenation in step ii) of the process of the invention is preferably conducted in the presence of a Pd catalyst comprising $SiO_2$, $Al_2O_3$ or mixtures of $SiO_2$ and $Al_2O_3$ as support material.

Accordingly, a preferred embodiment of the invention relates to a process as defined above in which, in step ii), a Pd catalyst comprising $SiO_2$ and/or $Al_2O_3$ as support material is used as catalyst.

With regard to the preferred and particularly preferred Pd content and/or support material and to the preferred and particularly preferred use amounts of the Pd catalyst used in step ii) in this embodiment, reference is made to the above remarks.

The oxidative dehydrogenation is typically effected in the liquid phase, meaning that the pressure and temperature for the conversion are chosen such that the feedstocks are in liquid form.

The temperature in the oxidative dehydrogenation is preferably within a range from 10 to 150° C., more preferably in the range from 20 to 130° C., especially in the range from 40 to 120° C.

The oxidative dehydrogenation can be effected at ambient pressure or reduced or elevated pressure. Preference is given to performing the oxidative dehydrogenation at elevated pressure. Particular preference is given to performing the oxidative dehydrogenation at a pressure in the range from 1 to 200 bar, more preferably from 1.5 to 100 bar, especially from 2 to 50 bar.

Typically, the oxidative dehydrogenation is effected in the presence of a gas mixture comprising 5% to 25% by volume of oxygen, i.e. in the presence of an oxygenous atmosphere.

The gas mixture used in step ii) of the process of the invention, comprising 5% to 25% by volume of oxygen, can be supplied to the reaction zone, for example, by a single injection prior to or on commencement of the reaction, by repeated injection during the reaction, or by continuous introduction over the entire course of the reaction. Preferably, in step ii) of the process of the invention, the oxygenous gas mixture is supplied to the reaction zone by continuous introduction over the entire course of the reaction.

Typically, gas mixture used in step ii) of the process of the invention comprises an oxygen content in the range from 5% to 25% by volume, preferably from 7% to 20% by volume and especially from 8% to 15% by volume.

In a particularly preferred embodiment of step ii) of the process of the invention, the oxygenous atmosphere is exchanged by supplying an oxygen-enriched gas mixture and removing an oxygen-depleted gas mixture. The supply and removal of the oxygen-enriched and oxygen-depleted gas mixtures can be effected successively or simultaneously. Preferably, the exchange of the oxygenous atmosphere is performed repeatedly, and the total amount of oxygenous gas mixture exchanged corresponds at least to the volume of the amount of gas present in the reaction zone. More preferably, the total amount of oxygenous gas mixture exchanged corresponds to several times the volume, for example 10 times the volume, of the amount of gas present in the reaction zone. The exchange can be effected stepwise or continuously. Preferably, the oxygenous atmosphere is exchanged continuously.

If the oxygenous atmosphere is exchanged continuously, the exchange rate of the oxygenous gas or gas mixture in the oxidative dehydrogenation is typically in the range from 1 to 200 L/h, preferably in the range from 3 to 120 L/h, especially in the range from 5 to 80 L/h, based on 100 g of the first product mixture used in step ii).

The oxidative dehydrogenation can be performed in the presence or absence of an added organic solvent.

If the oxidative dehydrogenation is performed in the presence of an added organic solvent, this is preferably an organic solvent which is inert under the reaction conditions, as already defined above for the catalytic isomerization.

Preference is given to adding no external organic solvent in the oxidative dehydrogenation.

After the oxidative dehydrogenation in step ii) of the process of the invention has ended, a second product mixture enriched in 3-methyl-2-butenal and depleted in 3-methyl-2-butenol compared to the first product mixture from step i) is generally obtained.

A rise in at least one of the reaction parameters, especially the reaction temperature, the pressure, the reaction time or residence time, or the amount of catalyst used, generally leads to an increase in conversion or to a higher content of 3-methyl-2-butenal in the reaction mixture for the oxidative dehydrogenation (second product mixture). However, losses in selectivity are to be expected owing to breakdown reactions and further reactions. Especially in the case of longer reaction times or residence times, there can be an increase in side reactions, for example overoxidation (increased formation of acids, epoxides, rearrangement products and the like). More particularly, this can lead to an increase in the formation of isoamyl alcohol, which can be separated from the reaction mixture only with difficulty.

For this reason, the reaction parameters in the oxidative dehydrogenation, especially the amount of catalyst, the pressure, the reaction temperature and the reaction time or residence time, are generally chosen such that the proportion of 3-methyl-2-butenal in the second product mixture is typically in the range from 2% to 55% by weight, preferably in the range from 10% to 45% by weight and especially in the range from 15% to 35% by weight, based on the total weight of the second product mixture.

The oxidative dehydrogenation in step ii) of the process of the invention is typically run such that the molar ratio of 3-methyl-2-butenol to 3-methyl-2-butenal in the second product mixture is in the range from 75:25 to 35:65, preferably in the range from 70:30 to 40:60 and especially in the range from 65:35 to 45:55.

The second product mixture thus obtained, after subsequent removal of the Pd catalyst used and after a distillative removal of at least some of the 3-methyl-3-butenol present in the second product mixture, can be used directly as a feedstock for preparation of isoprenoid materials of value, for example for preparation of odorants, for example citral, or vitamins, for example vitamin E and vitamin A.

In a preferred embodiment of the process of the invention, the oxidative dehydrogenation in step ii) is additionally performed in the presence of a base. Suitable bases which can be used in the oxidative dehydrogenation are mineral bases, especially the hydroxides of the alkali metals and alkaline earth metals, for example LiOH, NaOH, KOH, RbOH, CsOH, $Mg(OH)_2$ or $Ca(OH)_2$. More preferably, the base used in the oxidative dehydrogenation is selected from NaOH and KOH.

The proportion of the base in the reaction mixture is in the range from 0.01% to 2% by weight, more preferably in the range from 0.05% to 1.5% by weight, especially in the range from 0.1% to 1% by weight, based on the amount of the first product mixture used in step ii).

In a specific embodiment of the process of the invention, the oxidative dehydrogenation of the first product mixture obtained in step i), as defined above, is performed over a $SiO_2/Al_2O_3$-supported Pd catalyst or over a carbon-supported Pd/Au catalyst in the presence of a gas mixture comprising 8% to 15% by volume of oxygen, and in the presence of 0.1% to 1% by weight of KOH or NaOH, based on the amount of the first product mixture used, and at a temperature in the range from 40 to 120° C. and a pressure in the range from 2 to 50 bar, in such a way that a second product mixture comprising 3-methyl-2-butenol and 3-methyl-2-butenal in a molar ratio in the range from 70:30 to 40:60 is obtained.

In a particularly preferred embodiment of steps i) and ii) of the process of the invention, the oxygen content of the gas mixture used in step i) is 2% to 10% by volume, preferably 3% to 8% by volume, especially 4% to 6% by volume, below the oxygen content of the gas mixture used in step ii).

In a further particularly preferred embodiment of the process of the invention, in steps i) and ii), an oxygen-enriched gas mixture is supplied continuously to the respective reaction zones and an oxygen-depleted reaction mixture is removed continuously. The continuous supply of the oxygen-enriched gas mixture to the respective reaction zones can be effected in various ways. Preference is given to the continuous supply of the oxygen-enriched gas mixture below the liquid surface of the respective reaction mixtures.

In a specific embodiment of the process of the invention, in steps i) and ii), an oxygen-enriched gas mixture is supplied continuously to the respective reaction zones and an oxygen-depleted gas mixture is removed continuously, wherein the supply of the oxygen-enriched gas mixture is below the liquid surface of the respective reaction mixtures.

Distillative Separation

In a further embodiment of the process of the invention, the second product mixture obtained in step ii) is subjected to a distillative separation into a product fraction enriched in 3-methyl-2-butenol and 3-methyl-2-butenal and a reactant fraction enriched in 3-methyl-3-butenol.

Suitable apparatuses for distillative separation of the second product mixture obtained in step ii) are all apparatuses for distillative separation of reaction mixtures comprising liquid components. Suitable apparatuses include distillation columns such as tray columns, which may be equipped with bubble-cap trays, sieve plates, sieve trays, structured packings or random packings, or spinning band columns, evaporators such as thin film evaporators, falling film evaporators, forced circulation evaporators, Sambay evaporators etc., and combinations thereof. Particular preference is given to accomplishing the distillative separation of the composition obtained in step ii) using distillation columns and/or spinning band columns, especially spinning band columns.

In the distillative separation, a vapor is first drawn off from the second product mixture obtained in step ii), and is subsequently at least partly condensed. Condensation or partial condensation of the vapor can be accomplished using any suitable condensers. These can be cooled with any desired cooling media. Condensers with air cooling and/or water cooling are preferred, and air cooling is particularly preferred.

The product fraction enriched in 3-methyl-2-butenol and 3-methyl-2-butenal which is obtained after the distillative separation can subsequently, according to the desired degree of purity, be subjected to further purification steps, such as distillation or the customary liquid chromatography methods that are familiar to the person skilled in the art. In general, the product fraction enriched in 3-methyl-2-butenol and 3-methyl-2-butenal which is obtained after the distillative separation can be used directly for preparation of isoprenoid materials of value, for example for preparation of odorants, for example citral, or vitamins, for example vitamin E and vitamin A.

The reactant fraction enriched in 3-methyl-3-butenol which is obtained after the distillative separation can be used as feedstock in the catalytic isomerization in step i). For this purpose, fresh, i.e. pure commercially available 3-methyl-3-butenol is optionally added to this fraction enriched in 3-methyl-3-butenol. If the catalytic isomerization is conducted continuously, fresh 3-methyl-3-butenol is generally added to the reactant fraction enriched in 3-methyl-3-butenol which is used in step i), in which case the amount of fresh 3-methyl-3-butenol added typically corresponds to the amount of fresh 3-methyl-3-butenol which is expected to be converted in the catalytic isomerization and the subsequent oxidative dehydrogenation in step ii).

Continuous Performance

The process of the invention can be performed batchwise or in continuous mode. Preferably, at least one of steps i) and ii) of the process of the invention is conducted continuously. In a particularly preferred embodiment of the process of the invention, both steps i) and ii) are conducted continuously.

The catalyst hourly space velocity in the oxidative dehydrogenation is typically in the range from 0.1 to 50 kg of 3-methyl-2-butenal per kg of catalyst arid hour, preferably from 0.2 to 30 kg of 3-methyl-2-butenal per kg of catalyst and hour, and especially in the range from 0.5 to 15 kg of 3-methyl-2-butenal per kg of catalyst and hour.

In continuous mode, the process of the invention can be conducted in one or more reactors. Preference is given to performing the process in at least two reactors connected to one another in the form of a cascade.

If the two process steps are conducted continuously, the catalytic isomerization and the oxidative dehydrogenation are conducted in parallel but spatially separately from one another in at least one reactor each.

For example, the catalytic isomerization as defined above is effected in a first reactor. The first product mixture thus obtained, optionally with removal of the catalyst in solid form, is fed as a continuous product stream directly to the oxidative dehydrogenation that proceeds in parallel with the catalytic isomerization in a second reactor. At the same time, the first reactor is supplied continuously with 3-methyl-3-butenol, as defined above, in order to keep the volume of the reaction solution in the first reactor constant. The second product mixture which is enriched in 3-methyl-2-butenal and depleted in 3-methyl-2-butenol compared to the first product mixture and is obtained after the oxidative dehydrogenation in the second reactor is withdrawn from, the second reactor as product stream and can be supplied as feedstock, after the catalyst has been removed, to further processes as described above.

The invention is illustrated in detail by the examples described hereinafter. At the same time, the examples should not be regarded as a restriction of the invention.

In the examples which follow, the following abbreviations are used:

Offgas mode represents a reaction regime with exchange of the oxygenous atmosphere, i.e. continuous introduction of an oxygen-enriched (fresh) gas mixture with simultaneous continuous removal of an oxygen-depleted (spent) gas mixture;

offgas represents the amount of oxygenous gas mixture exchanged;

MBE represents isoprenol (3-methyl-3-butenol);

SAP represents an $SiO_2/Al_2O_3$-supported Pd catalyst.

EXAMPLES

In the examples, the following catalysts were used:

| | |
|---|---|
| 5% Pd-C WET reduced (BASF-Italia) | Moist and pre-reduced Pd catalyst from BASF Italia with activated carbon as support material and a Pd content of 5%. |
| 5% Pd-C WET reduced Escat (STREM) | Moist and pre-reduced Pd catalyst from Strem with the brand name Escat, comprising activated carbon as support material and having a Pd content of 5% and a water content of 50%. |
| 10% Pd-C WET reduced Escat (STREM) | Moist and pre-reduced Pd catalyst from Strem with the brand name Escat, comprising activated carbon as support material and having a Pd content of 10%. |
| 5% Pd-C WET reduced (AlfaAesar) | Moist and pre-reduced Pd catalyst from AlfaAesar having a BET surface area of 900 to 1100 $m^2/g$, comprising activated carbon as support material and having a Pd content of 5% and a water content of 50%. |
| 5% Pd on barium sulfate reduced (Aldrich) | Pre-reduced Pd catalyst from Aldrich, comprising barium sulfate as support material and having a Pd content of 5%. |
| 5% Pd on $SiO_2$ dry reduced Escat (STREM) | Pre-reduced dry Pd catalyst from Strem with the brand name Escat, comprising silicon oxide as support material and having a Pd content of 5%. |
| 3% Pd SAP dry reduced (BASF-Italia) | Pre-reduced dry Pd catalyst from BASF Italia, comprising a mixed silicon/aluminum oxide as support material and having a Pd content of 3%. |
| 5% Pd on alumina reduced Escat (STREM) | Pre-reduced Pd catalyst from Strem with the brand name Escat, comprising aluminum oxide as support material and having a Pd content of 5%. |
| 4% Pd/4% Au on activated carbon | Pre-reduced Pd catalyst (non-commercial in-house BASF production), comprising activated carbon as support material and having a Pd content of 4% and an Au content of 4%. |

I) Catalytic Isomerization:

The individual experiments were generally conducted under oxygenous atmosphere in a pressure-stable reactor with a mechanical stirrer. Performance of the catalytic isomerization on a laboratory scale was accomplished using a 350 mL glass pressure vessel (DN 50 for 8 bar), equipped with a baffle, a heating apparatus (Huber Ministat 230-CC), a sparging stirrer (Pt 100, 7 bar safety valve, gas connections with QC quick-release couplings), a pressure reducer for the pressure range of 0-10 bar, and optionally a flowmeter at the gas inlet and a pressure regulator, i.e. pressure release valve, at the gas outlet.

Unless stated otherwise, the following standard conditions were used for the catalytic isomerization experiments which follow:

Stirrer speed: 1000 rpm

Exchange rate of oxygenous gas: 30 L/h

Reaction temperature: 80° C.

Pressure in the reactor: 5-20 bar

Amount of feedstock: 100 g

The catalytic isomerization experiments were conducted with various Pd catalysts. The results of the experiments are compiled in table 1.

TABLE 1

Catalytic isomerization

| Exp. no. | Catalyst | Pressure [bar] | O₂ cont. [%] | Offgas [L/h] | Temp. [° C.] | Reaction time [h] |
|---|---|---|---|---|---|---|
| 1 | 5% Pd—C WET reduced (BASF-Italia) | 5 | 5 | 30 | 80 | 5 |
| 2 | 5% Pd—C WET reduced (BASF-Italia) | 5 | 5 | 30 | 80 | 10 |
| 3 | 5% Pd—C WET reduced Escat (STREM) | 5 | 5 | 30 | 80 | 5 |
| 4 | 5% Pd—C WET reduced (AlfaAesar) | 5 | 5 | 30 | 80 | 5 |
| 5 | Reuse of the cat. from exp. no. 6 | 5 | 5 | 30 | 80 | 5 |
| 6 | 10% Pd—C WET reduced Escat (STREM) | 5 | 5 | 30 | 80 | 5 |
| 7 | 10% Pd—C WET reduced Escat (STREM) | 5 | 5 | 30 | 80 | 5 |
| 8 | 5% Pd—C WET reduced Escat (STREM) | 5 | 5 | 30 | 80 | 5 |
| 9 | 5% Pd—C WET reduced (AlfaAesar) | 5 | 5 | 30 | 80 | 10 |
| 10 | 5% Pd—C WET reduced (AlfaAesar) | 5 | 10 | 30 | 80 | 5 |
| 11 | 5% Pd—C WET reduced (AlfaAesar) | 5 | 10 | 30 | 80 | 5 |
| V1 [1] | 5% Pd on barium sulfate reduced (Aldrich) | 5 | 5 | 30 | 80 | 5 |
| V2 [1] | 3% Pd SAP dry reduced (BASF-Italia) | 5 | 5 | 30 | 80 | 5 |
| V3 [1] | 3% Pd SAP dry reduced (BASF-Italia) | 5 | 10 | 30 | 80 | 5 |
| V4 [1] | 5% Pd on SiO₂ dry reduced Escat (STREM) | 5 | 10 | 30 | 80 | 5 |

| Exp. no. | MBE [% by wt.] | Prenol [% by wt.] | Prenal [% by wt.] | Total [% by wt.] | MBE conversion [%] | Sel. for prenol [%] | Sel. for prenal [%] | Yield of prenol [%] | Yield of prenal [%] |
|---|---|---|---|---|---|---|---|---|---|
| 1 | 39.99 | 54.07 | 4.46 | 98.52 | 60.17 | 89.50 | 7.56 | 53.85 | 4.55 |
| 2 | 32.64 | 55.69 | 7.39 | 95.72 | 67.62 | 81.70 | 11.10 | 55.24 | 7.51 |
| 3 | 47.09 | 49.88 | 3.48 | 100.44 | 53.00 | 93.90 | 6.71 | 49.78 | 3.56 |
| 4 | 45.48 | 50.24 | 3.70 | 99.42 | 54.66 | 91.60 | 6.91 | 50.09 | 3.78 |
| 5 | 44.86 | 50.17 | 4.00 | 99.03 | 55.27 | 90.50 | 7.39 | 50.02 | 4.08 |
| 6 | 42.68 | 53.10 | 1.14 | 96.92 | 57.36 | 92.05 | 2.05 | 53.05 | 1.17 |
| 7 | 41.13 | 52.15 | 4.23 | 97.51 | 58.99 | 88.10 | 7.32 | 51.99 | 4.32 |
| 8 | 38.80 | 54.69 | 5.07 | 98.56 | 61.24 | 89.20 | 8.47 | 54.64 | 5.19 |
| 9 | 40.45 | 47.64 | 6.38 | 94.47 | 59.71 | 79.50 | 10.90 | 47.45 | 6.51 |
| 10 | 31.27 | 53.11 | 8.58 | 92.97 | 68.76 | 77.20 | 12.76 | 53.06 | 8.78 |
| 11 | 33.92 | 51.52 | 7.78 | 93.21 | 66.15 | 77.70 | 12.02 | 51.42 | 7.95 |
| V1 [1] | 99.51 | 0.09 | 0.43 | 100.00 | 1.19 | 7.50 | 36.84 | 0.09 | 0.44 |
| V2 [1] | 98.00 | 0.02 | 0.49 | 98.51 | 2.69 | 0.70 | 18.55 | 0.02 | 0.50 |
| V3 [1] | 90.06 | 0.67 | 0.78 | 91.52 | 10.39 | 6.40 | 7.65 | 0.67 | 0.79 |
| V4 [1] | 94.30 | 0.61 | 0.64 | 95.54 | 6.27 | 9.70 | 10.39 | 0.61 | 0.65 |

[1] Comparative experiment

As apparent from table 1, carbon-supported Pd catalysts show thee desired activity. In general, total selectivities, i.e. the selectivities of prenol and prenal together, of more than 90% are attained. It was possible to successfully implement recycling of the catalyst and subsequent reuse. In addition, it was generally possible to identify a decline in the formation of isoamyl alcohol by virtue of the reaction conditions used; the values were in a range of 0.5-1.0 area %.

Table 2 shows the profile of the conversion of MBE against time and the amount of prenol and prenal formed in a representative catalytic isomerization reaction.

TABLE 2

Profile of the catalytic isomerization against time

| Exp. no. | Catalyst | Pressure [bar] | O₂ content [%] | Offgas [L/h] | Temperature [° C.] | Reaction time [h] |
|---|---|---|---|---|---|---|
| 12 | 5% Pd—C WET reduced (AlfaAesar) | 5 | 5 | 30 | 80 | 1 |
| | | | | | | 2 |

TABLE 2-continued

Profile of the catalytic isomerization against time 3
4
5

| Exp. no. | MBE [% by wt.] | Prenol [% by wt.] | Prenal [% by wt.] | Total [% by wt.] | MBE conversion [%] | Sel. for prenol [%] | Sel. for prenal [%] | Yield of prenol [%] | Yield of prenal [%] |
|---|---|---|---|---|---|---|---|---|---|
| 12 | 90.10 | 8.70 | 0.91 | 99.71 | 10.44 | 82.80 | 8.87 | 8.65 | 0.93 |
|  | 59.14 | 37.18 | 2.19 | 98.51 | 41.21 | 89.70 | 5.41 | 36.96 | 2.23 |
|  | 47.76 | 48.04 | 3.25 | 99.04 | 52.53 | 90.90 | 6.30 | 47.75 | 3.31 |
|  | 39.38 | 54.54 | 4.32 | 98.24 | 60.86 | 89.10 | 7.22 | 54.21 | 4.40 |
|  | 33.29 | 57.67 | 5.67 | 96.62 | 66.91 | 85.70 | 8.62 | 57.32 | 5.77 |

As can be inferred from table 2, after a reaction time of about 3 h, the highest values for selectivity for prenol are obtained at an MBE conversion of more than 50%.

The outputs from the isomerization can be used in the oxidative dehydrogenation without further purification. According to the reaction profile and reaction time, this gives rise to differences in the composition of the reaction feeds.

II) Oxidative Dehydrogenation of Outputs from the Catalytic Isomerization:

The feedstocks used in the oxidative dehydrogenation experiments which follow were outputs from the catalytic isomerization that were conducted analogously to the experiments detailed under I). These isomerization outputs, after removal of the catalyst, were used directly in the oxidative dehydrogenation without conducting an intermediate purification.

The individual oxidative dehydrogenation experiments were generally conducted under oxygenous atmosphere in a pressure-stable reactor with a mechanical stirrer. By comparison with the catalytic isomerization, the experiments were all conducted at a higher $O_2$ content (10% by volume), preferably 5% higher. Unless stated otherwise, the following standard conditions were used for the oxidative dehydrogenation experiments which follow:

Stirrer speed: 1000 rpm
Exchange rate of oxygenous gas: 30 L/h
Reaction temperature: 80° C.
Pressure in the reactor: 5-20 bar
Amount of feedstock: 100 g The oxidative dehydrogenation experiments on the isomerization outputs from I) were conducted with the catalysts 3% Pd SAP dry reduced (BASF-Italia) and 4% Pd/4% Au on activated carbon.

Tables 3 and 4 summarize the results from the oxidative dehydrogenation experiments with direct use of outputs from catalytic isomerizations. Tables 3 and 4 each list, in the upper part of the line (t=0), the composition of the isomerization outputs used, meaning that the values reported for t=0 correspond to the composition of the isomerization output used in each case. The different composition and total proportions of MBE, prenol and prenal in the isomerization outputs is attributable to different reaction conditions, such as different residence times, performance of catalyst recycling or other variations in the catalytic isomerization performed in each case.

TABLE 3

Oxidative dehydrogenation of isomerization outputs. Catalyst: 3% Pd SAP dry reduced (BASF-Italia); addition: 0.2% NaOH.

| Exp. no. | Feed: | Amount of cat. [g] | Pressure [bar] | $O_2$ cont. [%] | Offgas [L/h] | Temp. [° C.] | Reaction time [h] |
|---|---|---|---|---|---|---|---|
| 13 | Output 1 | 1.25 (fresh) | 20 | 10 | 30 | 80 | 0 |
|  |  |  |  |  |  |  | 2 |
| 14 | Output 2 | 1.25 (fresh) | 20 | 10 | 30 | 60 | 0 |
|  |  |  |  |  |  |  | 5 |
| 15 | Output 3 | 1.25 (from exp. no. 15) | 20 | 10 | 30 | 60 | 0 |
|  |  |  |  |  |  |  | 5 |
| 16 | Output 4 | 1.25 (from exp. no. 16) | 20 | 10 | 30 | 60 | 0 |
|  |  |  |  |  |  |  | 2 |
| 17 | Output 5 | 1.25 (from exp. no. 16) | 20 | 10 | 30 | 70 | 0 |
|  |  |  |  |  |  |  | 2 |
| 18 | Output 6 | 1.25 (from exp. no. 17) | 5 | 10 | 30 | 60 | 0 |
|  |  |  |  |  |  |  | 5 |
| 19 | Output 7 | 1.25 (fresh) | 20 | 10 | 30 | 80 | 0 |
|  |  |  |  |  |  |  | 2 |
| 20 | Output 8 | 1.25 (from exp. no. 20) | 20 | 10 | 30 | 80 | 0 |
|  |  |  |  |  |  |  | 2 |

TABLE 3-continued

Oxidative dehydrogenation of isomerization outputs. Catalyst:
3% Pd SAP dry reduced (BASF-Italia); addition: 0.2% NaOH.

| Exp. no. | Prenol [% by wt.] | Prenal [% by wt.] | MBE [% by wt.] | Total [% by wt.] | H$_2$O content [%] | MBE conversion [%] | Sel. for prenol [%] | Sel. for prenal [%] | Sel. for Total [%] |
|---|---|---|---|---|---|---|---|---|---|
| 13 | 52.1 | 7 | 35.5 | 94.6 | n.d. | 67.3 | 80.5 | 10.2 | 90.7 |
|  | 34.6 | 25.4 | 27.2 | 87.2 | 6.5 | 72.5 | 48.2 | 34.5 | 82.7 |
| 14 | 49.6 | 8.5 | 34.6 | 92.7 | n.d. | 65.4 | 75.8 | 12.7 | 89 |
|  | 41.7 | 15.5 | 32.5 | 89.6 | 5.8 | 67.2 | 62.7 | 22.8 | 85 |
| 15 | 53.6 | 7.3 | 33.2 | 94.1 | n.d. | 66.8 | 80.2 | 10.7 | 90.9 |
|  | 21.8 | 39.8 | 20.8 | 82.4 | n.d. | 78.5 | 28.9 | 51.5 | 80.3 |
| 16 | 52.7 | 7.4 | 38.8 | 98.9 | n.d. | 63.5 | 78 | 10.7 | 88.7 |
|  | 35.7 | 23.4 | 27.9 | 86.9 | 7.7 | 73.1 | 47 | 30.1 | 77.1 |
| 17 | 54.1 | 7.6 | 33.8 | 95.5 | n.d. | 66.3 | 81.5 | 11.2 | 92.7 |
|  | 33.8 | 25.9 | 24 | 83.7 | 9.1 | 75.3 | 46.2 | 34.6 | 80.8 |
| 18 | 42.9 | 50.1 | 5.1 | 98.1 | n.d. | 58.2 | 84 | 8.3 | 92 |
|  | 35.7 | 23.3 | 29.4 | 88.3 | n.d. | 71.1 | 49.4 | 31.6 | 81 |
| 19 | 40.4 | 5.4 | 52.3 | 98.1 | n.d. | 47.8 | 84.7 | 11 | 95.7 |
|  | 32.5 | 11.2 | 45.9 | 89.6 | 2.3 | 54.2 | 62.6 | 21.1 | 83.7 |
| 20 | 46 | 6.6 | 40.8 | 93.4 | n.d. | 59.3 | 77.4 | 10.8 | 88.2 |
|  | 28.9 | 26.2 | 28.84 | 83.9 | 7.7 | 71.3 | 42.9 | 38 | 80.9 |

TABLE 4

Oxidative dehydrogenation of isomerization outputs. Catalyst:
4% Pd/4% Au on activated carbon, addition: 0.2% NaOH.

| Exp. no. | Feed: | Amount of cat. [g] | Pressure [bar] | O$_2$ cont. [%] | Offgas [L/h] | Temp. [° C.] | Reaction time [h] |
|---|---|---|---|---|---|---|---|
| 21 | Output 9 | 1.25 (fresh) | 5 | 10 | 30 | 80 | 0 5 |
| 22 | Output 10 | 1.25 (fresh) | 5 | 10 | 30 | 60 | 0 6 |
| 23 | Output 11 | 1.25 (fresh) | 20 | 10 | 30 | 60 | 0 5 |
| 24 | Output 12 | 1.25 (fresh) | 20 | 10 | 30 | 80 | 0 6.25 |
| 25 | Output 13 | 1.25 (fresh) | 5 | 10 | 30 | 60 | 0 2 |
| 26 | Output 14 | 1.25 (from exp. no. 23) | 5 | 10 | 30 | 60 | 0 2 |

| Exp. no. | Prenol [% by wt.] | Prenal [% by wt.] | MBE [% by wt.] | Total [% by wt.] | H$_2$O cont. [%] | MBE conversion [%] | Sel. for prenol [%] | Sel. for prenal [%] | Sel. for Total [%] |
|---|---|---|---|---|---|---|---|---|---|
| 21 | 56.60 | 5.70 | 34.10 | 96.40 | n.d. | n.d. | n.d. | n.d. | n.d. |
|  | 38.50 | 25.10 | 23.90 | 87.50 | 4.20 | n.d. | n.d. | n.d. | n.d. |
| 22 | 50.80 | 7.00 | 37.00 | 94.80 | n.d. | n.d. | n.d. | n.d. | n.d. |
|  | 45.50 | 19.40 | 26.30 | 91.20 | n.d. | n.d. | n.d. | n.d. | n.d. |
| 23 | 54.2 | 7.7 | 32.7 | 94.6 | n.d. | 68 | 77.6 | 9.9 | 87.4 |
|  | 45.4 | 20.5 | 21.9 | 87.8 | 5.9 | 78.4 | 57.1 | 25.1 | 82.3 |
| 24 | 58.10 | 7.60 | 29.90 | 95.60 | n.d. | n.d. | n.d. | n.d. | n.d. |
|  | 25.80 | 33.60 | 18.70 | 78.10 | 9.10 | n.d. | n.d. | n.d. | n.d. |
| 25 | 52.60 | 6.80 | 36.80 | 96.20 | n.d. | n.d. | n.d. | n.d. | n.d. |
|  | 44.50 | 16.90 | 25.60 | 87.00 | n.d. | n.d. | n.d. | n.d. | n.d. |
| 26 | 51.30 | 6.40 | 38.80 | 96.50 | n.d. | 61.30 | 83.50 | 10.10 | 93.60 |
|  | 37.90 | 22.40 | 25.60 | 85.90 | 6.60 | 74.2 | 51.5 | 29.7 | 81.2 |

The direct use of the outputs from the catalytic isomerization in the oxidative dehydrogenation is possible since there is obviously no catalyst poison formed in the catalytic isomerization. Recycling experiments (up to 4×) were successful both for the 3% Pd SAP catalyst used and for the 4% Pd/4% Au catalyst. It is even possible to observe an increase in the activity here. The raising of temperature, pressure and residence time generally leads to an increase in yield, but losses of selectivity have to be expected owing to breakdown reactions and further reactions, for example overoxidation.

III) Oxidative Dehydrogenation of a Mixture of Prenol and MBE and of Pure Prenol:

In table 6 are the results from oxidative dehydrogenation experiments on a specific mixture of prenol and MBE and, as a comparative experiment, on pure prenol. The values listed under t=0 in table 5 correspond to the amount of the feedstock used in each case or of the composition of the feedstocks used in each case. 3% Pd SAP dry reduced (BASF-Italia) was used as catalyst. All experiments were run with 30 L/h of offgas and 0.2% NaOH. Otherwise, the standard conditions specified under II) were used. The total selectivity reported corresponds to the sum total of the selectivities of prenol and prenal.

TABLE 5

Oxidative dehydrogenation of a specific mixture of prenol and MBE and of pure prenol.
Catalyst: 3% Pd SAP dry reduced (BASF-Italia); addition: 0.2% NaOH.

| Exp. no. | Feed: | Amount of cat. [g] | Pressure [bar] | $O_2$ cont. [%] | Offgas [L/h] | Temp. [° C.] | Reaction time [h] |
|---|---|---|---|---|---|---|---|
| 27 | MBE/prenol mixture | 1.25 (fresh) | 20 | 10 | 30 | 80 | 0 |
|  |  |  |  |  |  |  | 2 |
| V5 [1)] | Pure prenol | 1.25 (fresh) | 20 | 10 | 30 | 80 | 0 |
|  |  |  |  |  |  |  | 2 |

Oxidative dehydrogenation of various 3-methyl-2-butenol-containing feedstocks.
Catalyst: 3% Pd SAP dry reduced (BASF-Italia); addition: 0.2% NaOH.

| Exp. no. | Prenol [% by wt.] | Prenal [% by wt.] | MBE [% by wt.] | Total [% by wt.] | $H_2O$ cont. [%] | MBE conversion [%] | Sel. for prenol [%] | Sel. for prenal [%] | Sel. for Total [%] |
|---|---|---|---|---|---|---|---|---|---|
| 27 | 65 | 0 | 35 | 100 | n.d. | 65 | 100 | 0 | 100 |
|  | 44.2 | 24.5 | 24 | 89.9 | 6.6 | 75.5 | 62.2 | 29.1 | 91.3 |
| V5 [1)] | 100 | 0 | 0 | 100 | n.d. | 100 | 100 | 0 | 100 |
|  | 46.5 | 20.1 | 19 | 85.7 | 6 | 81 | 59.5 | 25.1 | 84.7 |

[1)] Comparative experiment

The experiments show that high total selectivities (91%) can be achieved in the oxidative dehydrogenation with mixtures of MBE/prenol (pure). The use of pure prenol, by contrast, led only to a total selectivity of about 85%. This is in agreement with findings from blank experiments which showed that prenol can break down very quickly in the presence of oxygen. The use of the original output from the catalytic isomerizations gives comparable results to a synthetic MBE/prenol mixture. The use of an MBE/prenol mixture is thus found to be advantageous.

The invention claimed is:

1. A process for preparing a composition comprising 3-methyl-2-butenol and 3-methyl-2-butenal, comprising
    i) subjecting 3-methyl-3-butenol to a catalytic isomerization over a carbon-supported Pd catalyst in the presence of a gas mixture comprising 1% to 15% by volume of oxygen to obtain a first product mixture comprising at least 40% by weight of 3-methyl-2-butenol, at least 5% by weight of 3-methyl-3-butenol and 0% to 15% by weight of 3-methyl-2-butenal, based on the total weight of the first product mixture,
    ii) subjecting the first product mixture obtained in step i) to an oxidative dehydrogenation over a Pd catalyst comprising $SiO_2$ and/or $Al_2O_3$ as support material, or over a carbon-supported Pd/Au catalyst in the presence of a gas mixture comprising 5% to 25% by volume of oxygen, to obtain a second product mixture which is enriched in 3-methyl-2-butenal and depleted in 3-methyl-2-butenol compared to the first product mixture, where the molar ratio of 3-methyl-2-butenol to 3-methyl-2-butenal in the second product mixture is in the range from 75:25 to 35:65,
    wherein the oxidative dehydrogenation in step i) is conducted in the presence of a base.

2. The process according to claim 1, wherein the catalyst used in step ii) is a Pd catalyst comprising $SiO_2$ and/or $Al_2O_3$ as support material.

3. The process according to claim 1, wherein the gas mixture used in step i) comprises 3% to 10% by volume of oxygen.

4. The process according to claim 1, wherein the gas mixture used in step ii) comprises 8% to 15% by volume of oxygen.

5. The process according to claim 1, wherein the oxygen content of the gas mixture used in step i) is 2% to 10% by volume below the oxygen content of the gas mixture used in step ii).

6. The process according to claim 1, wherein the first product mixture obtained in step i) consists of
    i.1 40% to 80% by weight of 3-methyl-2-butenol,
    i.2 0% to 15% by weight of 3-methyl-2-butenal,
    i.3 5% to 59% by weight of 3-methyl-3-butenol and
    i.4 0% to 10% by weight of compounds other than i.1, i.2 and i.3.

7. The process according to claim 1, wherein the first product mixture obtained in step i) consists of
    i.1 45% to 70% by weight of 3-methyl-2-butenol,
    i.2 5% to 10% by weight of 3-methyl-2-butenal,
    i.3 20% to 50% by weight of 3-methyl-3-butenol and
    i.4 0% to 5% by weight of compounds other than i.1, i.2and i.3.

8. The process according to claim 1, wherein the total proportion of 3-methyl-2-butenol, 3-methyl-2-butenal and 3-methyl-3-butenol in the first product mixture obtained in step i) is at least 80% by weight, based on the total weight of the first product mixture.

9. The process according to claim 1, wherein step i) is conducted without supply of an external solvent.

10. The process according to claim 1, wherein the catalytic isomerization of 3-methyl-3-butenol in the presence of oxygen is run up to a conversion of 30% to 80%, based on the 3-methyl-3-butenol used.

11. The process according to claim 1, wherein the output from the catalytic isomerization, optionally after removal of the catalyst, is used without further purification in the oxidative dehydrogenation in step ii).

12. The process according to claim 1, wherein the proportion of the base in the reaction mixture is 0.01% to 2% by weight, based on the total weight of the first product mixture used in step ii).

13. The process according to claim 1, wherein step ii) is conducted without supply of an external solvent.

14. The process according to claim 1, wherein, in steps i) and ii), an oxygen-enriched gas mixture is supplied continuously to the respective reaction zones and an oxygen-depleted gas mixture is removed continuously, wherein the supply of the oxygen-enriched gas mixture is below the liquid surface of the respective reaction mixtures.

15. The process according to claim 1, wherein the process is performed continuously.

16. The process according to claim 1, wherein the second product mixture obtained in step ii) is subjected to a distillative separation into a product fraction enriched in 3-methyl-2-butenol and 3-methyl-2-butenal and a reactant fraction enriched in 3-methyl 3-butenol.

17. The process according to claim 16, wherein the reactant fraction enriched in 3-methyl-3-butenol, optionally with addition of fresh 3-methyl-3-butenol, is used in step i).

* * * * *